United States Patent [19]

Bjurling et al.

[11] Patent Number: 4,864,178
[45] Date of Patent: Sep. 5, 1989

[54] ULTRASONIC PROBE FOR TESTING THE MATERIAL OF SLOTTED OR HOLLOW PIECES OF THE MATERIAL

[76] Inventors: Per A. Bjurling, Arrendebostaden Fridlevstad, 370 30 Rodeby; Martin Ryf, Grondalsv 177, 117 46 Stockholm; Goran P. Embring, Lyckvagen 1, 430 22 Varobacka, all of Sweden

[21] Appl. No.: 169,888

[22] Filed: Mar. 18, 1988

Related U.S. Application Data

[63] Continuation-in-part of Ser. No. 937,210, Dec. 3, 1986, abandoned.

[30] Foreign Application Priority Data

Dec. 6, 1985 [SE] Sweden .................................. 8505778

[51] Int. Cl.⁴ ............................................. H01L 41/08
[52] U.S. Cl. .................................... 310/334; 310/335; 310/336; 310/367; 73/642; 73/644; 73/661
[58] Field of Search .............................. 310/334–336, 310/367, 368; 73/618–624, 627–629, 632, 642, 644, 661

[56] References Cited

U.S. PATENT DOCUMENTS

| | | | |
|---|---|---|---|
| 3,159,023 | 12/1964 | Steinbrecher | 310/335 |
| 4,361,044 | 11/1982 | Kupperman et al. | 73/642 X |
| 4,388,831 | 6/1983 | Sherman | 73/623 |
| 4,430,593 | 4/1984 | Gohlert et al. | 310/334 X |
| 4,577,505 | 2/1986 | Jestrich et al. | 310/336 X |
| 4,593,568 | 6/1986 | Telford et al. | 73/623 |
| 4,619,143 | 10/1986 | Franklen | 73/623 X |
| 4,640,131 | 2/1987 | Kroning et al. | 73/644 |
| 4,641,529 | 2/1987 | Lorenzi et al. | 73/644 X |
| 4,699,150 | 10/1987 | Kawabuchi et al. | 73/644 X |
| 4,763,513 | 8/1958 | Zacharias | 310/335 X |

FOREIGN PATENT DOCUMENTS

| | | | |
|---|---|---|---|
| 0242322 | 12/1985 | Japan | 73/661 |
| 951277 | 3/1964 | United Kingdom | 73/644 |

Primary Examiner—Mark O. Budd

[57] ABSTRACT

An ultrasonic probe 1 for non-destructive material testing of slotted or hollowed pieces of material 2 and comprising a carrier 3 and a probe part 4 connected to said carrier, which probe part is formed with one or several piezo-electric crystals 5 provided at or adjacent the tip thereof and mounted at an angle to the longitudinal plane of the probe of between 45° and 50° and rotated around its own axis over an angle of about 45°–47°. The probe can be formed with two or several symmetrically arranged piezo-electric crystals for allowing a complete testing of the piece of material by one single docking operation in that the different crystals are connected in turn after each other. Further the probe may also be formed with one or several straight scanning piezo-electric crystals 6 mounted in the carrier 3.

5 Claims, 3 Drawing Sheets

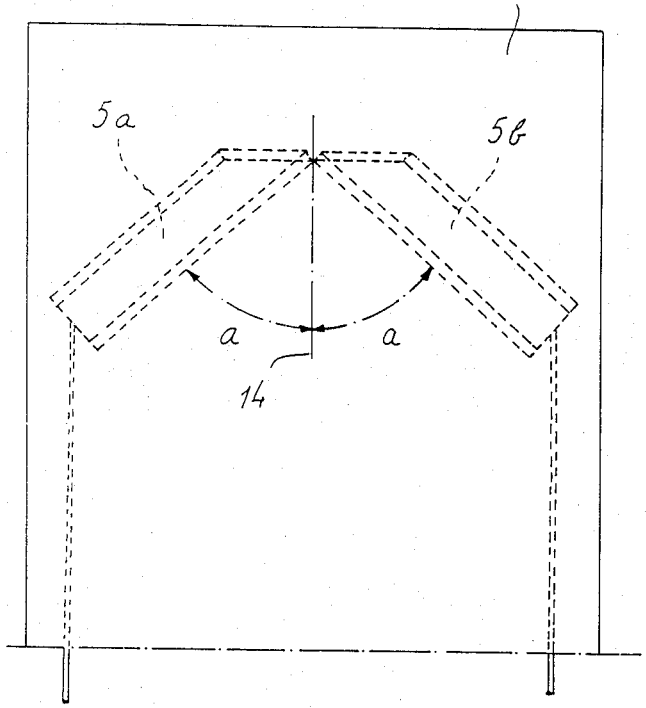
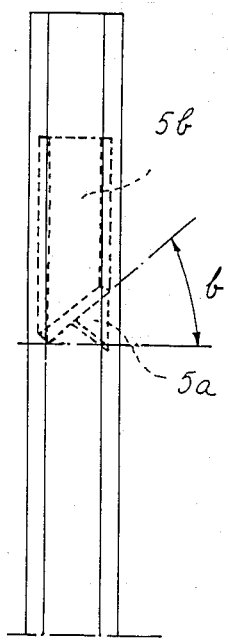
Fig. 3
Fig. 4
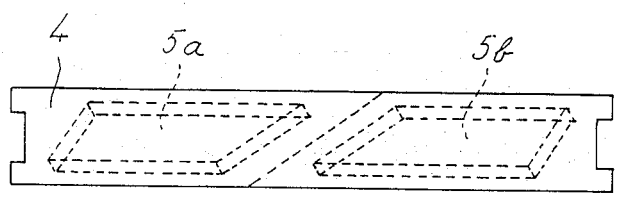
Fig. 5

ULTRASONIC PROBE FOR TESTING THE MATERIAL OF SLOTTED OR HOLLOW PIECES OF THE MATERIAL

CROSS REFERENCE TO RELATED APPLICATIONS

This application is a continuation-in-part of application Ser. No. 937,210, filed Dec. 3, 1986 now abandoned.

SUMMARY OF THE INVENTION

The present invention generally relates to non-destructive subsurface material testing by means of ultrasonic probes thereby detecting possible defects like fissures, pits, cavities etc. by observing differences from normal acoustic properties of pieces of materials caused by such defects. More particularly the invention is directed to testing slotted or hollow pieces of material.

The invention has been made especially in connection to testing the material of slotted guide pins for guide support tubes for fuel elements of a nuclear reactor, and in the description to follow the invention will be described with reference thereto. It is however, obvious that the invention is also for testing slotted or hollow pieces of other types as well, and that the invention is not restricted to the above mentioned specific technical field.

Ultrasonic probes for non-destructive testing of material are known, which may comprise a piezo-electric crystal or a piezo-electric element which when receiving a push of current emits sound waves of ultrashort wave length, for instance 2–4 MHz which sound waves are re-intercepted by the piezo-electric crystal and which upon analysis give an indication of the character of the material. In case there are fissures or cavities etc. in the material an acoustic impulse echo or an acoustic abnormality is observed, the magnitude and location of which can be calculated for instance with the experienced knowledge of the acoustic picture of a reference object which has been proved to be free from defects. Generally the testing is made so that several reference objects are analysed by means of an ultrasonic probe, both fault free objects and objects in which defects have been provided, and the acoustic pictures thereof are transmitted to an oscilloscope from which photos are preferably taken of the pictures, or the pictures are registered in any other way, so that remaining picture of the fault free reference objects and of the reference object having intentionally providing defects are obtained. Then the test objects are examined by means of the same ultrasonic probe, whereby the acoustic picture is registered on tape or directly on an oscilloscope and is compared with corresponding pictures of the reference objects. Possible defects appear in the form of large or small differences, generally peaks on the oscilloscope, the location of which, as compared with the reference picture, defines the place of defect of the object.

Known ultrasonic probes have been formed as contact probes which are applied directly into surface contact or nearly surface contact with the object to be tested. A known ultrasonic probe for testing for instance guide pins of guide support tubes for fuel elements of a nuclear reactor comprises a metal pin having a flat end adjacent to which one or two piezo-electric crystals or elements are inserted electrically isolated. The piezo-electric crystals are over conduits connected to a source both for emitting a push of current which in turn makes the crystal emit the ultrasound, and also for receiving current variation corresponding to the travel and return travel of the ultrasound through the test object.

This known ultrasonic probe, which is applied in direct contact with the test object and which during the testing is kept in close contact therewith is disadvantageous among other things, in that the sound with a slight side deflection is transmitted straight down in the test object, and it can be difficult or impossible to provide an all around extending scanning of the test object. Therefore it is necessary to make a large number of tests with different positions of the probe in order to obtain a fairly safe judging of the test object, and in spite of several tests there is a risk that the probe does not observe the defects in some parts of the test objects. Sometimes it may also be necessary to make several different tests with several different types of ultrasonic probes applied on different places. The known method and the known ultrasonic probes are time consuming and make great demands on the test equipment. Many times the sound also must be transmitted long ways through the test objects, which may lead to a damping of the sound and the corresponding faded signal observation, and as a consequence there may be difficulties in observing and localized defects. The problem is especially noticable in slotted or hollow test objects in which defects generally appear adjacent the root of the slots or in the transition area between the web and the flange portions of the test object.

The object of the invention therefore is to solve the problem or providing an ultrasonic probe by means of which it is possible to make a complete material testing in one single operation, preferably of a slotted or hollow piece of material and by means of which a stringent and cumulated picture is obtained of defects present in the test object.

According to the invention the ultrasonic probe comprises a carrier and from said carrier and extended rod form part the size and shape of which, as seen in cross section, substantially corresponds to the slot or the cavity of the test object, and at or adjacent the end of said rod or tip at least one or preferably at least two piezo-electric crystals or elements which are mounted in a predetermined position in relation to each other.

In order to obtain such a complete ultrasonic testing as possible by means of only one, two or several piezo crystals it is necessary that said crystal or crystals are mounted very specifically. Intensive tests have shown that the piezo-electric crystal or crystals preferably are mounted both at an angle in relation to the longitudinal axis of the rod part and also rotated around its own longitudinal axis. By such placing of the piezo-electric crystals or elements it is possible to provide a complete or nearly unitary transmitting of ultrasonic waves round the entire piece of material to be tested.

By forming the sound rotatable around its own axis it is in some cases possible to provide a good result with a probe having only one piezo-electric crystal. In many cases, for instance when the probe has a chisel-form or a similar form it is not possible to rotate the probe, and in such case the probe must be formed with at least two piezo-electric crystals each covering an angle of at least 180°, whereby the crystals are mounted in a specific way, so that the crystals together give a complete picture all around the test object.

In a preferred embodiment of the invention for testing slotted pieces of material the ultrasonic probe is chisel-formed and at or close to the tip or the end of the chisel-form rod part the probe has two separate piezo-electric crystals which are mounted at an angle of about 35°-70° or preferably 45° in two opposite directions in relation to the longitudinal axis of the rod part, and in addition thereto the crystals are rotated around its own axis at an angle of around 45°-50° in relation to the longitudinal axis of the rod part. A crystal which in relatively fine grain test objects prove to have a good distribution and a good signal-to-noise-ratio has a frequency of about 4 MHz. The said crystal, however, is not particularly suitable for course grain object, and tests have shown that a crystal having a frequency of about 2 MHz, in spite of giving a relatively less good distribution and signal-to-noise-ratio than the 4 MHz crystal still gives an ultrasound picture in course grain materials which is more easy to interprete. Therefore piezo-electric crystals having a frequency of about 4 MHz ought to be used as far as possible, but if the sound picture indicates that the test object is of course grain type crystals having a frequency of about 2 MHz should rather be used.

The crystals ought to be as large as possible, and preferably the crystals of the same probe out to overlap the axial center line of the test object of the longitudinal direction.

The only crystal in circular cylindric probes or the two or more crystals in other types of probes each are connected to a current giving and registering equipment over a conduit, whereby each crystal can transmit sound waves and receive reflected sound waves ord order to observe defects around half of the object. In a further preferred embodiment of the invention the ultrasound probe, in addition to the two or more crystals at the tip of the rod part, also is formed with two separate so-called straight observing crystals at the transition section between the carrier and the rod part, which crystals are likewise connected to the current emitting and registering equipment each over a conduit for separating observing the ultrasound picture from each crystal or element.

At the testing operation the crystals are one by one in turn after each other connected to the oscilloscope or the registering equipment thereby giving a separate sound picture for each separate crystal. The testing can be made in one single step only by changing connection in a connection box between several crystals.

Further characteristics of the invention and advantages thereof will be evident from the following detailed specification in which reference will be made to the accompanying drawings.

DESCRIPTION OF THE DRAWINGS

FIG. 3 is an enlarged detail of the ultrasonic probe according to FIG. 1 as seen from one side.

FIGS. 4 and 5 show the same detail seen from another side and top respectively.

DETAILED DESCRIPTION

Figures 1, 2:
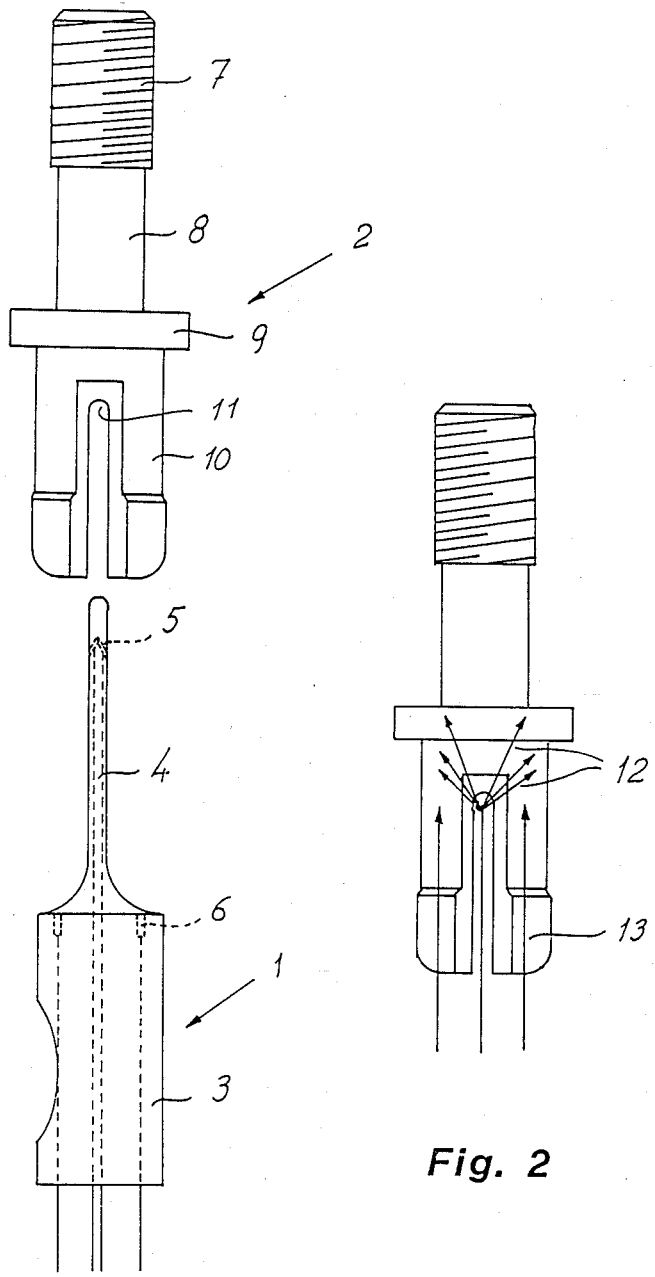
FIG. 1 shows an example of an ultrasound probe for testing a slotted guide pin of guide support tubes for fuel rods of a nuclear reactor.
FIG. 2 diagrammatically illustrates the general sound way for the piezo-electric elements at the tip of the ultrasonic probe of FIG. 1.

FIG. 1 shows a chisel formed ultrasonic probe 1 for testing a slotted pin, for instance a guide pin. The probe comprises a carrier 3 and a chisel part 4 adjacent the tip of which two "round scanning" piezo-electric crystals 5 are mounted. At the end of the carrier part 3 the probe may also be formed with two "straight scanning" crystals 6.

The slotted pin 2 is formed with threads 7, a web part 8, a flange 9 and the very slotted guide part 10 with the slot 11. In this type of pin it may be expected that defects like fissures or cracks appear both in the transition section between the web 8 and the flange 9 and also at the root of the slot 11. Of course there may be some defects internally in the material. In order to firstly observe the first mentioned defects two piezo-electric crystals adjacent the ends of the chisel part 4 are used, which crystals are mounted so as to give a round scanning or angle scanning substantially as shown with the arrows 12 of FIG. 2. Each crystal scans at least half the periphery of the pin 2.

The probe rod with the piezo-electric crystals should have such dimensions as to fit the slot or bore in which the probe is to be introduced for the material testing with only some few tenth of a millimiter play.

As a supplemental part for the round scanning crystals 5 the probe also may have a couple of straight scanning crystals 6 scanning the bolt in the axial direction substantially shown with the arrows 13 of FIG. 2.

Each "round" scanning crystal 5A and 5B in FIGS. 3, 4 and 5 is generally rectangular in configuration and has a thickness to dictate its frequency (smaller thicknesses providing higher frequencies and thick crystals lower frequencies). This thickness is constant throughout the crystal as suggested in these views, and each crystal further includes planar exterior surfaces that are parallel to one another and to a major element axis oriented at an angle (a) relative to the longitudinal axis 14 of the chisel part 4. The two parallel longer edges or edge surfaces are oriented parallel this major axis. The two shorter edges of the crystal are not parallel to one another although one edge adjacent the edge of an associated or adjacent crystal is oriented in alignment with the associated shorter edge of the adjacent crystal as suggested in FIG. 3 and also in FIG. 5. These shorter edges are referred to as the "near" shorter edges while the more remote shorter edges are generally perpendicular to the longer edges of the crystals and as illustrated in FIG. 4 these shorter edges are parallel to a minor axis of each crystal oriented perpendicular to its major axis. More particularly this minor axis is oriented at an angle (b) relative to the parallel faces of the chisel part 4 again as best shown in FIG. 4.

The angle (a) is preferably on the order of 46° relative the longitudinal axis of the probe or chisel part 4 and the angle (b) of the minor element axis is preferably oriented at 46.5° relative to the line normal to the faces of the chisel part 4.

The locating and positioning of the piezo-electric round scanning crystals 5 is critical and is shown diagrammatically in the enlarged picture of FIGS. 3 and 4. The crystals are mounted isolated in a damping block, and they are localized in an angle a of between 40° and 70° or preferably between 40° and 50° in relation to the longitudinal axis 14 of the chisel part 4, and they are also rotated in an angle b around its own axis of between 45 and 50°. Practical tests have shown that the optimum angles vary for different crystals. For instance a crystal of 4 MHz gives the best values at an angle a of about 50° and an angle b of about 45°, whereas a crystal of 2 MHz frequency gives the best result at an angle a of 46° and an angle b of about 46.5°. The two crystals 5a and 5b are isolated from each other, and each is connected to a mixing box 15 over a (not illustrated) conduit, and the mixing box 15 in turn is connected to an ultrasonic apparatus 16 having an oscilloscope like reading instrument 17. A computer or a tape registering unit 18 also may be connected to the ultrasonic apparatus 16. With the assistance of the mixing box 15 each of the piezo-electric crystals can in turn be connected and be read whereby a cumulated total sound picture is obtained of the four illustrated units, which picture is compared with corresponding reference pictures over fault free reference objects or reference objects having known defects thereby giving a clear conception of the character of the test object. Any fissures, cavities or similar defects given an echo which is observed as a peak on the oscilloscope 17.

Figures 6, 7:
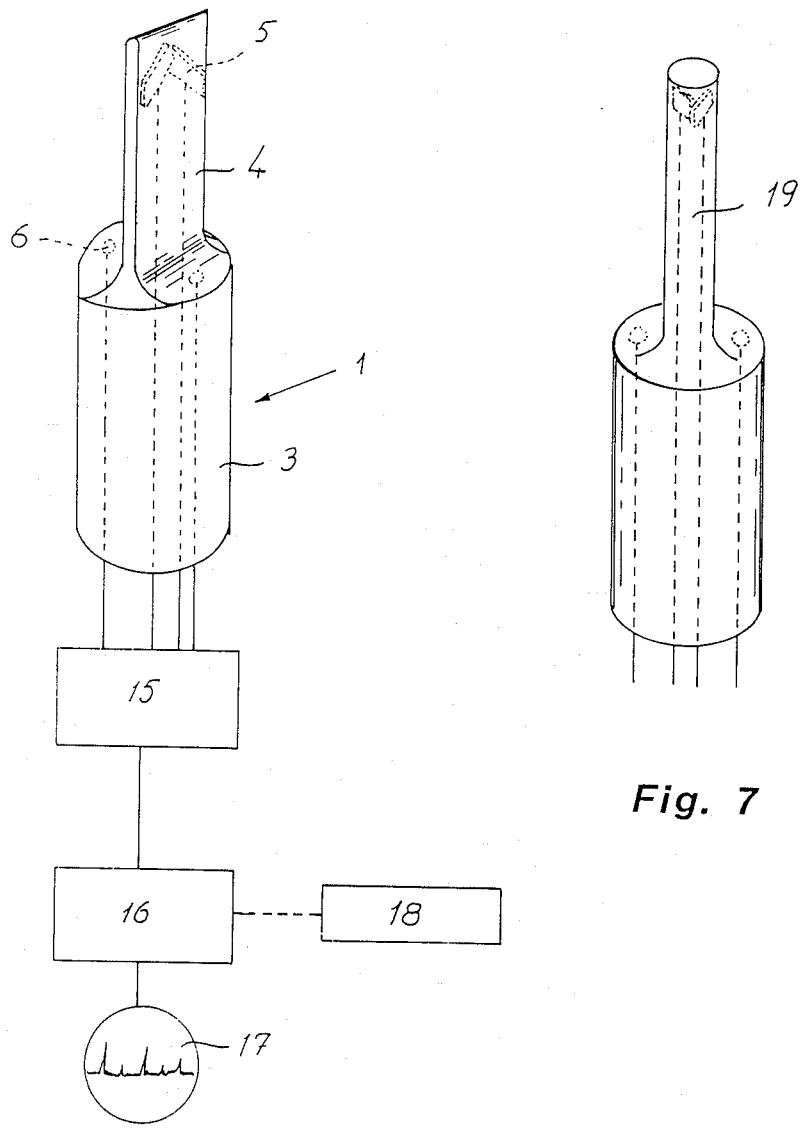
FIG. 6 shows a modified embodiment of an ultrasonic probe of the type shown in FIG. 1.
FIG. 7 shows and ultrasonic probe according to the invention intended for testing the material of test pieces formed with cylindric bores.

As previously mentioned the ultrasonic probe can be formed with a circular cylindrical probe part 19 as shown in FIG. 7 and at the tip of said cylindrical part 19 the probe is formed with one or several piezo-electric crystals. Irrespective of the number of crystals which are used said crystals ought to be placed as mentioned above at an angle a to the longitudinal axis of 40°–70° or preferably 45°–50° and rotated an angle b around its own longitudinal axis of about 45°. In case the probe has only one crystal this is provided centrally in the cylindric part and close to the tip thereof, and when making tests with such a probe it is rotated into several test steps, for instance 180°, 90° or any other angle, whereby a test is made in each such angular position. In case the probe is formed with two or several crystals they are mounted symmetrically according to the above mentioned guide lines.

We claim:

1. An ultransonic probe for use in a slotted specimen of bifurcated shape to provide an ultrasound trace of the specimen in the area adjacent the inner end of the slot, said probe comprising a carrier (3), a chisel shaped probe part (4) connected to the carrier and having a longitudinal axis, said probe part having a tip adapted for docking adjacent the inner end of the slot, said chisel shaped part having flat sides spaced from one another by a dimension dictated by the slot width, at least one piezo-electric crystal element provided adjacent the tip of said chisel shaped probe part, said piezo-electric crystal element having a generally rectangular planar shape and said element having a major element axis parallel the element's longer rectangular sides, and a minor element axis perpendicular said major element axis, said crystal element oriented in said probe part with said major element axis set at an angle (a) of about 46° relative said probe part longitudinal axis, and said element axis and longer sides defining a plane that is tilted relative said flat sides of said probe part so that a normal to said flat sides describes an angle (b) of about 46.5° with respect to said minor element axis.

2. An ultrasonic probe according to claim 1 further characterized by a second piezo-electric crystal element arranged in axially symetric relation to said one element in said tip such that both elements are arranged on opposite sides of said longitudinal axis at angles of 46°.

3. An ultrasonic probe according to claim 2 wherein said second element is provided in a second plane such that a normal to said flat probe part sides describes an angle (b) of 46.5° with said second element minor axis.

4. An ultrasonic probe for use in a hollow specimen defining a cylindrical bore to provide an ultrasound trace of the specimen in the area adjacent the inner end of the bore, said probe comprising a carrier, a cylindrical part (19) connected to the carrier and having a longitudinal axis, said cylinder probe part having a tip adapted for docking adjacent the inner end of the bore, said cylindrical probe part having a diameter dictated by the bore diameter, at least one piezo-electric crystal element provided adjacent the tip of said probe part, said element having a major element axis parallel the element's longer rectangular sides, and a minor element axis perpendicular said major element axis said crystal element oriented in said part with said element axis set at an angle (a) of about 50° relative said probe part longitudinal axis, and said major element axis and longer sides defining a plane that is tilted relative said longitudinal probe part axis so that said plane is inclined relative to a diameter of said probe part at an angle (b) of about 50° relative said minor element axis.

5. The ultrasonic probe according to claim 4 further characterized by a second piezo-electric crystal element arranged in axially symetric relation to said one element in said probe tip such that both elements have their major axes on opposite sides of said longitudinal axis at angles of 50° relative said longitudinal axis.

* * * * *